United States Patent
Zhao et al.

(10) Patent No.: US 12,297,424 B2
(45) Date of Patent: May 13, 2025

(54) PSEUDOMONAS FLUORESCENS N1 AND USE THEREOF

(71) Applicant: SHANXI BOYU BIOTECHNOLOGY CO., LTD., Taiyuan (CN)

(72) Inventors: Yu Zhao, Beijing (CN); Ying Zhang, Beijing (CN); Tiegen Zhang, Beijing (CN); Changxi Gong, Beijing (CN)

(73) Assignee: SHANXI BOYU BIOTECHNOLOGY CO., LTD., Taiyuan (CN)

( * ) Notice: Subject to any disclaimer, the term of this patent is extended or adjusted under 35 U.S.C. 154(b) by 0 days.

(21) Appl. No.: 18/752,770

(22) Filed: Jun. 24, 2024

(65) Prior Publication Data

US 2024/0368537 A1    Nov. 7, 2024

Related U.S. Application Data

(63) Continuation of application No. PCT/CN2022/126107, filed on Oct. 19, 2022.

(30) Foreign Application Priority Data

Oct. 26, 2021 (CN) .............. 202111251300
Feb. 7, 2022 (CN) .............. 202210116969

(51) Int. Cl.
| | | |
|---|---|---|
| C12N 1/20 | (2006.01) | |
| B09B 3/60 | (2022.01) | |
| B09C 1/10 | (2006.01) | |
| C05B 13/02 | (2006.01) | |
| C05F 7/00 | (2006.01) | |
| C05F 17/20 | (2020.01) | |
| C12R 1/39 | (2006.01) | |

(52) U.S. Cl.
CPC ............. *C12N 1/205* (2021.05); *B09B 3/60* (2022.01); *B09C 1/10* (2013.01); *C05B 13/02* (2013.01); *C05F 7/00* (2013.01); *C05F 17/20* (2020.01); *C12R 2001/39* (2021.05)

(58) Field of Classification Search
None
See application file for complete search history.

(56) References Cited

FOREIGN PATENT DOCUMENTS

| CN | 102108299 | * | 6/2011 |
|---|---|---|---|
| CN | 103864484 | | 6/2014 |
| CN | 106565012 | * | 4/2017 |
| CN | 109942347 | * | 6/2019 |
| CN | 110982727 | * | 4/2020 |
| CN | 111011159 B | | 11/2021 |
| CN | 114134069 | | 3/2022 |
| CN | 114480194 | | 5/2022 |

OTHER PUBLICATIONS

Kang, H., Liu, X., Zhang, Y., Zhao, S., Yang, Z., Du, Z., & Zhou, A. (2019). Bacteria solubilization of shenmu lignite: influence of surfactants and characterization of the biosolubilization products. Energy Sources, Part A: Recovery, Utilization, and Environmental Effects, 43(10), 1162-1180. (Year: 2019).*
Merck. ("Particle Size Conversion Table") Retrieved 2024. URL: https://www.sigmaaldrich.com/US/en/support/calculators-and-apps/particle-size-conversion-table?srsltid=AfmBOoq9qfqzwPJY2a1nQploB07K3Z2OJM1Kml-TTY7wQzcGCaEHihSp (Year: 2024).*
Fan ("Evaluating heavy metal accumulation and potential risks in soil-plant systems applied with magnesium slag-based fertilizer") (Year: 2018).*
Park ("Mechanism of insoluble phosphate solubilization by Pseudomonas fluorescens RAF15 isolated from ginseng rhizosphere and its plant growth-promoting activities"). (Year: 2009).*
International Search Report for International Application No. PCT/CN2022/126107 mailed on Dec. 1, 2022 (Chinese original).
Written Opinion for International Application No. PCT/CN2022/126107 mailed on Dec. 1, 2022 (Chinese original).
Search Report for Chinese Application No. 2021112513003, mailed on Jun. 7, 2022 (Chinese original).
First Office Action for Chinese Application No. 2021112513003, mailed on Jun. 7, 2022 (Chinese original).
Supplementary Search Report for Chinese Application No. 2021112513003, mailed on Jun. 27, 2022 (Chinese original).
Notice of Patent Grant for Chinese Application No. 2021112513003, mailed on Jun. 27, 2022 (Chinese original).
Search Report for Chinese Application No. 202210116969X, mailed on Jun. 29, 2022 (Chinese original).
Notice of Patent Grant for Chinese Application No. 202210116969X, mailed on Jun. 29, 2022 (Chinese original).
Rawat, P. et al., Phosphate-Solubilizing Microorganisms: Mechanism and Their Role in Phosphate Solubilization and Uptake, Journal of Soil Science and Plant Nutrition, vol. 21, Sep. 30, 2020, pp. 49-68.

(Continued)

*Primary Examiner* — Holly Kipouros
*Assistant Examiner* — Nathan G Esperon
(74) *Attorney, Agent, or Firm* — Addison D. Ault; IPGentleman Intellectual Property Services, LLC

(57) ABSTRACT

This application relates to *Pseudomonas fluorescens* N1, and usage therefor in solid waste recycling based on full bionic simulation combined with a microorganism. Light, temperature, gas and heat conditions in cyclic transformation of organic carbon in soil are simulated, and solid waste is mixed and stacked in the soil or between hills, wherein the solid waste is basically blended according to the carbon-nitrogen ratio, alkalinity or acidity, and water content of the solid waste, and no turning is performed according to the principle of anaerobic fermentation. By introducing high-carbon, high-salt, alkaline or acidic liquid waste using a bionic head cover during stacking, the anaerobic fermentation process is controlled to stop at an acid production stage so that organic acids produced are fully mixed with the solid waste, and the nutrients in the solid waste are released by using acidic materials and thus become nutritional elements for acidic material chelation.

3 Claims, No Drawings

(56) References Cited

OTHER PUBLICATIONS

Wang, Jing, Passivation of Pb in Various Contaminated Soil by Phosphate Rock Combined with Phosphate-Solubilizing Bacteria, Chinese Doctoral Dissertations & Master's Theses Full-text Database(Master), Engineering Science and Technology I, No. 8, Aug. 15, 2020, abstract(para. 1 in pp. I and para. 3 in pp. II) (Chinese original).
Zhao, Y., et al., CN114134069A, English Machine translation, pp. 1-11, Mar. 4, 2022, Generated Jun. 12, 2024.
Zhao, Y., et al., CN114480194A, English machine translation, pp. 1-4, May 13, 2022, Generated Jun. 12, 2024.
Liu, Boqun et al., CN103864484A, English machine translation, pp. 1-2, Jun. 18, 2014, Generated Jun. 12, 2024.
Xie, Chengwei et al., CN110982727, English machine translation, pp. 1-2, Aug. 28, 2019, Generated Jun. 12, 2024.
International Search Report for International Application No. PCT/CN2022/126107 mailed on Dec. 1, 2022 (English translation generated Jun. 7, 2024).
Written Opinion for International Application No. PCT/CN2022/126107 mailed on Dec. 1, 2022 (English translation generated Jun. 7, 2024).
Search Report for Chinese Application No. 2021112513003, mailed on Jun. 7, 2022 (English translation generated Jun. 13, 2024).
First Office Action for Chinese Application No. 2021112513003, mailed on Jun. 7, 2022 (English translation generated Jun. 13, 2024).
Supplementary Search Report for Chinese Application No. 2021112513003, mailed on Jun. 27, 2022 (English translation generated Jun. 13, 2024).
Notice of Patent Grant for Chinese Application No. 2021112513003, mailed on Jun. 27, 2022 (English translation generated Jun. 13, 2024).
Search Report for Chinese Application No. 202210116969X, mailed on Jun. 29, 2022 (English translation generated Jun. 13, 2024).
Notice of Patent Grant for Chinese Application No. 202210116969X, mailed on Jun. 29, 2022 (English translation generated Jun. 13, 2024).
Wang, Jing, Passivation of Pb in Various Contaminated Soil by Phosphate Rock Combined with Phosphate-Solubilizing Bacteria, Chinese Doctoral Dissertations & Master's Theses Full-text Database(Master), Engineering Science and Technology I, No. 8, Aug. 15, 2020, abstract(para. 1 in pp. I and para. 3 in pp. II) (English translation generated Jun. 12, 2024).
Search Report for Chinese Application No. 2022111112378, mailed on Dec. 12, 2024.
English translation of Search Report for Chinese Application No. 2022111112378, mailed on Dec. 12, 2024.
First Office Action for Chinese Application No. 2022111112378, mailed on Dec. 16, 2024.
English translation of First Office Action for Chinese Application No. 2022111112378, mailed on Dec. 16, 2024.
Notice of Patent Grant for Chinese Application No. 2022111112378, mailed on Mar. 13, 2025.
English translation of Notice of Patent Grant for Chinese Application No. 2022111112378, mailed on Mar. 13, 2025.
English translation of CN111011159 B(PX) Nov. 5, 2021.

* cited by examiner

PSEUDOMONAS FLUORESCENS N1 AND USE THEREOF

TECHNICAL FIELD

This application relates to *Pseudomonas fluorescens* N1 and the use thereof and falls within the technical field of biologics.

BACKGROUND ART

Industrial and agricultural solid wastes have gradually become a world problem. By most of the world standards and national standards, landfill treatment is used, not only may have toxic substances leaked, but also leave the future of landslides, soil and water conservation and other hidden dangers. There is an urgent need for a method of disposal that can be consumed in large quantities. If these solid wastes can be substrate-treated, a great cycle of industrial, mining and agriculture will be realized, and toxic and hazardous substances therein can be subjected to phytoremediation by utilizing plant growth characteristics.

Magnesium slag contains a large amount of Ca, Si, Mg and other mineral elements required for plant growth, but the research reports on the agricultural resource utilization of magnesium slag are not many at present. Coal gangue, as a solid waste discharged in the process of coal mining and coal washing, is a kind of black and gray rock with lower carbon content and harder than coal that is accompanied by the coal seam in the process of coal formation. It is currently one of the largest solid wastes discharged in China and can cause serious environmental hazards if not handled properly. Coal gangue is rich in $SiO_2$, $Al_2O_3$, $Fe_2O_3$, CaO, and carbon, which provides the basis for its application in the chemical industry. However, the natural coal gangue has a dense structure and must first be modified to improve the activity of the coal gangue. The modification of coal gangue in the existing technology is mostly studied in chemical modification, and microbial modification is less studied.

Phosphate-solubilizing microorganisms undergo many different reactions to release phosphorus as they solubilize phosphate. According to the research, the phosphate-solubilizing mechanism of phosphate-solubilizing bacterium mainly includes the pH value of the surrounding environment, the secretion of organic acids and phosphatase secretion and the like, which mainly provide plants with phosphorus and thus promote plant growth. There are few reports of phosphate-solubilizing microorganisms in modifying coal gangue, and remediation of contaminated soil synergistically with other solid wastes such as magnesium slag to promote plant development.

SUMMARY

This application aims to address the shortcomings of the existing solid waste-reformed substrate mentioned above and develop *Pseudomonas fluorescens* N1 and a usage method therefor in modification of solid waste synergistically with coal gangue material. Functional microorganisms are used for solid waste reforming. Phosphate-solubilizing microorganisms are sprayed, which can change the acidity and alkalinity of the substrate solid waste raw materials. *Xanthomonas* is used for surface modification of the substrate solid waste raw materials, which changes the hydrophilicity of the solid waste. The carbon-nitrogen ratio within the substrate can be changed by adding agricultural waste for the substrate microecology. The phosphate-solubilizing microorganisms can be added for stable acid hydrolysis of agricultural waste to ensure sustainable plant growth.

Specifically, this application relates to *Pseudomonas fluorescens* N1 registered in the China General Microbiological Culture Collection Center under the accession number CGMCC No. 23192.

This application also relates to a method for modifying solid waste by microorganisms synergistically with coal gangue material, comprising the following steps:
(1) adding coal gangue to magnesium slag in an amount of 10-15% by volume of the magnesium slag, mixing thoroughly; sieving to control the particle size of the mixed material to be 2-5 mm, and stacking for 5-10 days:
(2) adding vinegar dregs in an amount of 20-30% by volume of the magnesium slag, mixing thoroughly; and adjusting the pH value to 5.5-6.5 using a wood vinegar liquid; and
(3) spraying phosphate-solubilizing bacterium *Pseudomonas fluorescens* and/or *Xanthomonas campestris* on the material surface, and spraying water in an amount of 0.50-1.00 $m^3/m^3$ material per day for 30-40 days.

Further, the coal gangue of step (1) is added in an amount of 13% by volume of the magnesium slag and is stacked for 8 days.

Further, the phosphate-solubilizing bacterium is preferably *Pseudomonas fluorescens*, and the *Xanthomonas* is preferably *Xanthomonas campestris*. The *Xanthomonas* is preferably *Xanthomonas campestris* NRRLB-1459, but is not limited to this species.

Further, the phosphate-solubilizing bacterium is preferably *Pseudomonas fluorescens* N1 registered in the China General Microbiological Culture Collection Center under the accession number CGMCC No. 23192.

This application also relates to a method for remedying heavy metal contaminated soil by a microorganism synergistically with coal gangue material, comprising the following steps:
(1) adding coal gangue to magnesium slag in an amount of 10-15% by volume of the magnesium slag, mixing thoroughly, sieving to control the particle size of the mixed material to be 2-5 mm, and stacking for 5-10 days:
(2) adding vinegar dregs or wood vinegar liquid to adjust the pH value to 5.5-6.5;
(3) spraying phosphate-solubilizing bacterium (*Pseudomonas fluorescens*) and/or *Xanthomonas* on the material surface, and spraying water in an amount of 0.50-1.00 $m^3/m^3$ material per day for 30-40 days.

Further, the coal gangue of step (1) is added in an amount of 15% by volume of the magnesium slag and is stacked for 10 days; and the pH value of step (2) is 5.5.

Further, the phosphate-solubilizing bacterium is preferably *Pseudomonas fluorescens*, and the *Xanthomonas* is preferably *Xanthomonas campestris*.

Further, the phosphate-solubilizing bacterium is preferably *Pseudomonas fluorescens* N1 registered in the China General Microbiological Culture Collection Center under the accession number CGMCC No. 23192. The *Xanthomonas* is preferably *Xanthomonas campestris* NRRLB-1459, but is not limited to this species.

This application also relates to a method for preparing a cultivation substrate from solid waste modified by a microorganism synergistically with coal gangue, comprising the following steps:

(1) adding coal gangue to magnesium slag in an amount of 10-15% by volume of the magnesium slag, mixing thoroughly, sieving to control the particle size of the mixed material to be 2-5 mm, and stacking for 5-10 days:

(2) adding vinegar dregs in an amount of 20-30% by volume of the magnesium slag, mixing thoroughly, and adjusting the pH value to 5.5-6.5 using a wood vinegar liquid; and (3) adding phosphate rock powder in an amount of 5-10% by volume of the total materials, and mixing thoroughly; and (4) spraying phosphate-solubilizing bacterium (*Pseudomonas fluorescens*)+*Xanthomonas* onto the material surface, adjusting the carbon-nitrogen ratio to about 25:1, spraying water in an amount of 0.50-1.00 $m^3/m^3$ material per day for 30-40 days, so that the phosphate-solubilizing bacterium release organic acids continuously to form the substrate for cultivation.

Further, it can further comprise the following steps:

(5) placing the substrate in a seedling pot with an antiseepage membrane at the bottom, transplanting a plant, and filling slags with no porous between the seeding pots between the seedling pots to create a micromoisture-preservation environment that promotes rapid root growth; and (6) when a sprout is germinated or a new leaf is expanded, selling the plant or remedying the ecology in situ.

Further, the phosphate-solubilizing bacterium is preferably *Pseudomonas fluorescens* N1 registered in the China General Microbiological Culture Collection Center under the accession number CGMCC No. 23192. The *Xanthomonas* is preferably *Xanthomonas campestris* NRRLB-1459, but is not limited to this species.

In view of the above-mentioned background, this application develops a method for simulating a bionic swamp cover head and large-scale composting of solid waste substrate. By using the bionic cover head, the light, temperature, air, and heat conditions in the composting process of solid waste mixtures can be controlled, and the process of organic carbon formation in the environment can be simulated. The carbon-nitrogen ratio, pH change, salinity change, and water content inside the mixture can be determined by means of probes. The waste liquid can be injected by using the bionic swamp cover head to adjust the mixture's acid production fermentation conditions. Whether the acid production process is completed can be determined through the silicate resolution, acidic compound secretion, and soluble nutrient values inside the mixture. After completion, the substrate can be taken out for cultivating various crops.

Specifically, this application relates to a method for simulating the natural formation process of an organic carbon ore by using a biomimetic method, that combines the acid production conditions of biological fermentation, uses the carbon-nitrogen ratio, pH and salinity in the waste liquid to regulate the amount of acid production, and strips the silicate surface layer in the solid waste and activating various nutrient components.

This application also relates to a method for recycling solid waste based on full bionic simulation combined with a microorganism, wherein the microorganism is *Pseudomonas fluorescens* N1. The method includes the following steps:

(1) stacking coal gangue with a particle size of 2-5 mm at the bottom at a stacking thickness of 5-10 m:

(2) stacking a bionic swamp mixture, specifically a mixture of sludge, kitchen waste and fly ash on the first layer of coal gangue, and adjusting the water content of the mixture so that the fermentation water meets the basic requirements of anaerobic fermentation: at the same time, controlling the water content of the mixture to be 40%-60%, and adjusting the carbon-nitrogen ratio to be (25-35): 1, pH 4.6-6.0, salinity 20%-30%, and composting thickness 2-5 m, for anaerobic fermentation:

(3) repeating steps (1)-(2) alternately, and performing multi-layer composting according to a stacking treatment amount to improve stacking efficiency and a treatment total amount:

(4) laying a bionic swamp cover head on the uppermost layer of the stacked layer, wherein the bionic swamp cover head consists of the solid waste: during the anaerobic fermentation process, a functional microorganism eluent, a carbon-nitrogen ratio eluent, a pH value adjustment eluent and a high-salt eluent for the lower stacked layer can be transported via the bionic swamp cover head, and at the same time the use of the bionic swamp cover head to adjust the damp-heat energy storage of the bottom stacked layer can be facilitated; and providing a solar membrane for energy collection on the bionic swamp; and (5) providing an induction probe at the bottom of the bionic swamp cover head to feed back the temperature and humidity of the fermentation stack in time, and when the temperature is too high or too low; controlling the condition by delivering the eluent at a certain temperature.

Further, the coal gangue of step (1) may be replaced with coal gangue and magnesium slag; and the fly ash of step (2) may be replaced with desulfurized ash.

Further, in the bionic swamp mixture of step (2), the volume ratio of kitchen waste: sludge: fly ash (or desulfurized ash) is 10:5: 3; and the carbon-nitrogen ratio is adjusted to 35:1.

Further, the bionic swamp cover head of step (4) consists of straw, mushroom dregs, and garden waste, preferably straw and mushroom dregs.

Further, the temperature of step (5) is maintained at from 16° C. to 35° C.; and the humidity is maintained at from 40% to 60%.

Further, in the microorganism washing liquid of step (4), the microorganism is an acid-producing anaerobic fermentation microorganism, preferably *Pseudomonas fluorescens* N1, water is sprayed in an amount of 1.00 $m^3/m^3$ material per day for 50-60 days for the microorganism eluent: the carbon-nitrogen ratio cluent is a conventional solution with a carbon-nitrogen ratio of 35:1, and the rich carbon-nitrogen ratio ensures that the anaerobic fermentation can stay in the acid-producing stage; and the pH cluent is added according to the feedback from the probe, i.e., when the pH is less than 4.6, an alkaline waste solution is added, and when the pH is greater than 6.0, an acidic waste solution is added.

This application utilizes functional microorganisms to treat and blend the solid waste according to their acidity; alkalinity, nutrient specificity, hydrophilicity, particle size, micro-ecological adaptability, etc. and places them in a seedling pot with an anti-seepage membrane at the bottom for cultivation. While adapting to the rooting and rapid growth of plants, it is completely isolated from the surrounding soil until the solid waste substrate is wrapped by the plant root system. The content of various pollutants in the solid waste substrate is tested to meet national standards. The rooted plants are transplanted together with the seedling pot. After transplanting, according to different greening requirements, the bottom is opened with a sized hole, so that the main root system can root into the corresponding plot, thus fixing the plant, conducive to its upward elongation. The whisker root system can wrap the solid waste substrate to absorb and passivate the harmful substances in the substrate. The formed plant with the substrate can be moved at will, high in the survival rate, and can also be used in the local plot to form a landscape. Various types of solid waste will return to the land and nature through plant growth, achieving large-scale reduction of solid waste and various pollutant remediation by the plants.

This application mainly uses functional microorganisms as the main tool to modify solid waste raw materials. Based on an accurate understanding of functional microorganisms and continuous experimentation, the modified substrate raw materials can be flexibly combined to meet different plant stages and growth characteristics, similar to the principle of soil testing and formula fertilization. The resulting substrate material, formulated substrate, will greatly promote plant rooting and growth, with good sustainability, and provide a substrate platform for plant remediation. Good plant growth can bring better remediation effects. At the same time, the plants produced by this technology are wrapped in nutrient pots for production, without occupying farmland or excavating surface soil, which damages the original ecology of the nursery: They can be used for ecological remediation by filling untreated solid waste around the spacing of the plant in the nutrient pot, or be directly sold together with the substrate, becoming a high-value, high survival rate, soil ball plant for road greening and mining ecological remediation.

Advantageous Effects

1. We studied for the first time the method of turning solid waste into plant cultivation substrate through biological modification. Specifically, magnesium slag and coal gangue are crushed into a certain particle size, and their adsorption capacity can be significantly improved through the modification of phosphate-solubilizing microorganisms. The modified coal gangue can adsorb the phosphate in the solid waste, and then through the biodegradation of phosphate-solubilizing microorganisms, release a high concentration of effective phosphorus that can be directly utilized by plants. Phosphate-solubilizing microorganisms in modifying coal gangue and in remediation of polluted soil synergistically with other solid wastes such as magnesium slag and in promotion of the development of plants is the first time proposed in this application. We found that a large number of trace elements in magnesium slag that can be absorbed and utilized by plants are concentrated in insoluble silicates. By mixing with coal gangue and using the method of microbial modification, the insoluble salts in magnesium slag can be adsorbed by the modified coal gangue, and then degraded into soluble ions (K', Na, effective nitrogen, phosphorus and potassium, etc.) by the phosphate-solubilizing bacterium to be directly absorbed and utilized by plants.
2. Through the study, we further concluded that the factors affecting the remediation capacity of the solid waste-reformed substrate are mainly based on the particle size of the material, the amount of coal gangue addition, and the dosage of phosphate-solubilizing bacterium phosphate-solubilizing bacterium dosage. The optimal solution affecting the ability of the solid waste-reformed substrate to remedy heavy metal lead pollution is a mixed substrate of 5 mm crushed particle size, 15% coal gangue addition, and 1.00 $m^3/m^3$ phosphate-solubilizing bacterium dosage. The optimal solution affecting the phosphate-solubilizing effect of solid waste-reformed substrate is a mixed substrate of 2 mm crushed particle size, 13% coal gangue addition, and 1.00 $m^3/m^3$ phosphate-solubilizing bacterium dosage. The order of influence of each factor is the ability to remedy heavy metal lead pollution: coal gangue addition>crushed particle size>phosphate-solubilizing bacterium dosage. The phosphate-solubilizing effect of solid waste-reformed substrate: crushed particle size>phosphate-solubilizing bacterium dosage>coal gangue addition.
3. The organic acids produced by the phosphate-solubilizing bacterium in the process of growth and reproduction can not only reduce the pH value in the soil environment but also directly release the phosphorus in the fixed-state phosphate into the soil. We found that a large number of trace elements in magnesium slag that can be absorbed and utilized by plants are concentrated in insoluble silicates. By mixing with coal gangue and using the method of microbial phosphate-solubilizing modification, the insoluble salts in magnesium slag can be adsorbed by the modified coal gangue and then degraded into soluble ions (K+, Na+, effective nitrogen, phosphorus and potassium, etc.) by the phosphate-solubilizing bacterium to be directly absorbed and utilized by plants. Tests have demonstrated that phosphate-solubilizing bacterium can synergize with coal gangue-modified magnesium slag solid waste, thereby releasing phosphorus from fixed-state phosphate into the soil to be utilized by plants.
4. The organic acids such as acetic acid, lactic acid, malic acid, oxalic acid, succinic acid, citric acid and gluconic acid produced by the phosphate-solubilizing bacterium in the process of growth and reproduction can not only reduce the pH value of the soil environment to release phosphorus from fixed-state phosphate into the soil directly but also form chelates with iron, aluminum and other ions for the crops to absorb and utilize. Organic acids produced by the metabolism of phosphate-solubilizing bacterium can block soil phosphorus adsorption sites or increase phosphorus effectiveness by forming complexes with cations on the surface of soil minerals. *Xanthomonas* can produce large amounts of xanthan gum. This application finds for the first time that its use in conjunction with phosphate-solubilizing bacterium can promote the release of effective phosphorus in solid waste, and produce organic acids, with a better synergized effect for modifying magnesium slag solid waste with coal gangue. The improved solid waste can be made into a plant growth substrate to promote the growth of plants.
5. The content of different coal gangue can affect the effective phosphorus content of the substrate and the production of organic acids, and the effective phosphorus content of the substrate was higher in all the other experiments compared to Control 4 without added coal gangue. Among them, the best results were obtained when the coal gangue content was 10-15 volume parts. The adsorption capacity of coal gangue modified by microorganisms is very strong, and it directly releases phosphorus from the fixed-state phosphate. Glycolic acid is the most representative type of organic acid and one of the important organic acids required for plant growth. By synergistically modifying the solid waste magnesium slag and coal gangue with *Pseudomonas*

*fluorescens* and *Xanthomonas*, the organic acids in the solid waste are released, thus promoting plant growth. Compared to other microorganisms, they are not as effective in solubilizing phosphates and releasing organic acids as using the combination of *Pseudomonas fluorescens*+*Xanthomonas* of this application.
6. Different pH values have different effects on the phosphate-solubilizing effect of the strains. After 30 days of modification of solid waste, effective phosphorus content was highest at pH 5.5 and organic acid content was highest at pH 5.5. The results showed that the effect of phosphate-solubilizing and organic acid production is good in the acidic solid waste substrate environment.
7. This application is the first to use magnesium slags as a hydrophobic raw material and vinegar dregs as a hydrophilic raw material, and through the reasonable proportioning of the two materials, combined with the adjustment of particle size (2-5 mm), to achieve the water content and aeration of the substrate suitable for plant cultivation. The comparative example showed that the volume ratio of magnesium slags and vinegar dregs at 100:30 can achieve the best effect on the water content and aeration of the substrate. Compared with the magnesium slag solid waste without coal gangue, the substrate aeration can be significantly reduced, and compared with the magnesium slag solid waste without vinegar dregs, the substrate water content can be also significantly reduced.
8. This application concludes that the addition of a certain amount of phosphorus ore powder (8%) can further promote the efficacy of the phosphate-solubilizing bacterium, which can further degrade the insoluble phosphorus in its ore powder into soluble phosphate, which can be used as a substrate together with the solid waste, and provide sufficient elements for the plant cultivation substrate.
9. This application is the first to ferment solid waste based on a full bionic simulation swamp reaction and obtains the optimized parameters affecting the acid-producing reaction of solid waste. By continuously optimizing the parameters, it was concluded that the water content, salinity; and carbon-nitrogen ratio in the full bionic simulation swamp reaction are very important. The highest fermentation and decomposition effect can be achieved when the carbon-nitrogen ratio is adjusted to 35:1, salinity 20% and water content 60%. It indicates that the phosphate-solubilizing and promotion of organic acid production in an acidic solid waste substrate environment is effective. In the process, the effective phosphorus content and acid production are both high. At the same time, the parameter could maintain the acidic environment and promote the persistent decomposition effect of microorganisms.
10. Light, temperature, gas and heat conditions in the cyclic transformation of organic carbon in soil are simulated, and solid waste is mixed and stacked in the soil or between hills, wherein the solid waste is basically blended according to the carbon-nitrogen ratio, alkalinity or acidity, and water content of the solid waste, and no turning is performed according to the principle of anaerobic fermentation. By introducing high-carbon, high-salt, alkaline or acidic liquid waste using a bionic head cover during stacking and regulating the oxygen content, the anaerobic fermentation process is controlled to stop at an acid production stage so that organic acids produced are fully mixed with the solid waste, and the nutrients in the solid waste are released by using acidic materials and thus become nutritional elements for acidic material chelation, thereby finally achieving the aim of resource utilization of solid waste.

Deposit Information

Strain name: *Pseudomonas fluorescens*
Latin name: *Pseudomonas fluorescens*
Strain Number: N1
Depository: China General Microbiological Culture Collection Center
Abbreviation of depository institution: CGMCC
Address: NO. 1 West Beichen Road, Chaoyang District
Deposit date: Aug. 25, 2021
Registration No. of the depository center: CGMCC No. 23192

DETAILED DESCRIPTION OF THE INVENTION

The technical solutions in the embodiments of this application will be described clearly and completely. Obviously, the described embodiments are only a part of the embodiments of this application, rather than all the embodiments. Based on the embodiments in this application, all the other embodiments obtained by a person of ordinary skill in the art without manufacturing any inventive effort fall within the scope of protection of this application.

The technical principle of this application is: proportioning the raw material of pre-treated solid waste substrate according to the result of modification: following the basic nutrient principle, acidity; alkalinity, salinity value, hydrophilicity, carbon-nitrogen ratio, introducing the functional bacterial flora to regulate the micro-ecology of the root growth: using the seedling pot to hold the substrate and planting into the plant; and intensively piling up between the seedling pot and seedling pot and adding untreated solid waste substrate for gap filling appropriately to build a micro-soil moisture preservation environment, utilizing the maintenance of plant root microenvironment; and after new branches have sprouted, transplanting the plants with the seedling pot. Depending on the purpose of transplanting, the bottom of the seedling pot is opened with a sized hole. For conventional greening, the hole size is less than 5 centimeters to fix the plant. For soil and water conservation greening, the hole size is increased to 15 centimeters or more to release more roots. Most of the root system remains inside the solid waste substrate for adsorption and passivation of various types of polluted toxic and hazardous substances for phytoremediation.

The *Xanthomonas* of this application is *Xanthomonas campestris* NRRLB-1459, but is not limited to this species, all *Xanthomonas* thereof may fulfill this application. The *Pseudomonas* of this application is *Pseudomonas fluorescens* N1, but is not limited to this species, all *Pseudomonas* thereof may fulfill this application. The above strain should be adjusted to a concentration of roughly $10^9$ cells per milliliter (OD600=1.0).

Example 1: A Method for Modifying Solid Waste by a Microorganism Synergistically with Coal Gangue Material Included the Following Steps (1) Coal gangue was added to magnesium slag in an amount of 13% by volume of the magnesium slag and mixed thoroughly. The mixed material was sieved to control the particle size to be 2 mm and stacked for 8 days.
(2) Vinegar dregs were added in an amount of 20% by volume of the magnesium slag and mixed thoroughly. The pH value of the mixed material was adjusted to 5.5 using a wood vinegar liquid.
(3) *Pseudomonas fluorescens* N1 was sprayed on the material surface. Water was sprayed in an amount of 1.00 m$^3$/m$^3$ material per day for 35 days.

Example 2: A Method for Modifying Solid Waste by a Microorganism Synergistically with Coal Gangue Material Included the Following Steps (1) Coal gangue was added to magnesium slag in an amount of 13% by volume of the magnesium slag and mixed thoroughly. The mixed material was sieved to control the particle size to be 2 mm and stacked for 8 days.
(2) Vinegar dregs were added in an amount of 20% by volume of the magnesium slag and mixed thoroughly. The pH value of the mixed material was adjusted to 5.5 using a wood vinegar liquid
(3) *Xanthomonas campestris* was sprayed on the material surface. Water was sprayed in an amount of 1.00 m$^3$/m$^3$ material per day for 35 days.

Example 3: A Method for Modifying Solid Waste by a Microorganism Synergistically with Coal Gangue Material, Included the Steps of (1) Coal gangue was added to magnesium slag in an amount of 10% by volume of the magnesium slag and mixed thoroughly. The mixed material was sieved to control the particle size to be 2 mm and stacked for 8 days.
(2) Vinegar dregs were added in an amount of 30% by volume of the magnesium slag and mixed thoroughly. The pH value of the mixed material was adjusted to 5.5 using a wood vinegar liquid.
(3) *Pseudomonas fluorescens* N1+*Xanthomonas campestris* (mixed with equal solution volume) were sprayed on the material surface. Water was sprayed in an amount of 1.00 m$^3$/m$^3$ material per day for 35 days.

Example 4: A Method for Remedying Heavy Metal Contaminated Soil by a Microorganism Synergistically with Coal Gangue Material Included the Following Steps (1) Coal gangue was added to magnesium slag in an amount of 15% by volume of the magnesium slag and mixed thoroughly. The mixed material was sieved to control the particle size to be 5 mm and stacked for 10 days.
(2) Vinegar dregs or wood vinegar liquid was added to adjust the pH value to 5.5.
(3) *Pseudomonas fluorescens* N1 and *Xanthomonas campestris* (mixed with equal solution volume) were sprayed on the material surface. Water was sprayed in an amount of 1.00 m$^3$/m$^3$ material per day for 30 days.

Example 5: A Method for Preparing a Cultivation Substrate from a Solid Waste Modified by a Microorganism Synergistically with Coal Gangue Included the Following Steps (1) Coal gangue was added to magnesium slag in an amount of 10% by volume of the magnesium slag and mixed thoroughly. The mixed material was sieved to control the particle size to be 3 mm and stacked for 5 days.
(2) Vinegar dregs were added in an amount of 30% by volume of the magnesium slag and mixed thoroughly: The pH value of the mixed material was adjusted to 5.5 using a wood vinegar liquid. Wood vinegar liquid: pH 3.3, contains 53.0% total amino acids.
(3) Phosphate rock powder was added in an amount of 8% by volume of the total materials and mixed thoroughly.
(4) *Pseudomonas fluorescens* N1 and *Xanthomonas campestris* (mixed with equal solution volume) were sprayed on the material surface. The Carbon-nitrogen ratio was adjusted to about 25:1. Water was sprayed in an amount of 1.00 m$^3$/m$^3$ material per day for 30 days so that the phosphate-solubilizing bacterium could release organic acids continuously to form a cultivation substrate.

Further Optionally (5) the substrate was placed in a seedling pot and transplanted with a plant. Slags were filled with no porous between the seeding pots, a micro-moisture-preservation environment can be created to promote rapid root growth.
(6) When a sprout is germinated or a new leaf is expanded, the plant is sold or the ecology is remedied in situ.

The phosphate-solubilizing bacterium is preferably *Pseudomonas fluorescens*.

The *Xanthomonas* can be *Xanthomonas campestris*.

When the carbon-nitrogen ratio is adjusted in step (4), ammonia water and nitrogen fertilizer are selected as the nitrogen source, and straw agricultural waste is selected as the carbon source.

Step (4) further comprises, with reference to the content of the main nutrients in the substrate for cultivation, calculating and adding the corresponding nitrogen fertilizers (urea, KNO$_3$, NH$_4$H$_2$PO$_4$, etc.), phosphorus fertilizers (calcium superphosphate, etc. (cured phosphorus)+potassium dihydrogen phosphate), potassium fertilizers (KNO$_3$, KH$_2$PO$_4$, etc.) to the substrate.

Example 6: A Method for Recycling Solid Waste Based on Full Bionic Simulation Combined with a Microorganism Included the Following Steps (1) Coal gangue with a particle size of 3 mm was stacked at the bottom at a stacking thickness of 6 m.
(2) A bionic swamp mixture, specifically a mixture of sludge, kitchen waste and fly ash was stacked on the first layer of coal gangue, and the water content of the mixture was adjusted to 60% so that the fermentation water met the basic requirements of anaerobic fermentation. At the same time, the carbon-nitrogen ratio was adjusted to be 35:1, pH 5.5, salinity 20%, and composting thickness 3 m, for anaerobic fermentation.
(3) Steps (1)-(2) were repeated alternately and multi-layer composting was performed according to a stacking treatment amount to improve stacking efficiency and total treatment amount.
(4) A bionic swamp cover head was laid on the uppermost layer of the stacked layer, wherein the bionic swamp cover head consists of crushed straw and mushroom dregs mixed according to a volume ratio of 3:2, and the crushed particle size of the two components was 3 cm.

During the anaerobic fermentation process, a functional microorganism eluent, a carbon-nitrogen ratio eluent, a pH value adjustment eluent and a high-salt eluent for the lower stacked layer can be transported via the bionic swamp cover head, and at the same time the use of the bionic swamp cover head to adjust the damp-heat energy storage of the bottom stacked layer can be facilitated. A solar membrane for energy collection was provided on the bionic swamp. In the microorganism eluent, the microorganism was an acidogenic anaerobic fermentation microorganism, preferably *Pseudomonas fluorescens* N1. Water was sprayed in an amount of 1.00 m³/m³ material per day for 60 days.

(5) An induction probe was provided at the bottom of the bionic swamp cover head to feed back the temperature and humidity of the fermentation stack in time, and when the temperature is too high or too low; the condition was controlled by delivering the eluent at a certain temperature. The temperature was maintained at 30° C. and humidity was maintained at 60%.

Example 7: A Method for Recycling Solid Waste Based on Full Bionic Simulation Combined with a Microorganism Included the Following Steps (1) Coal gangue and magnesium slag with a particle size of 3 mm were stacked at the bottom, wherein the amount of the coal gangue addition was 10% of the volume of the magnesium slag. Then vinegar dregs were added in an amount of 30% by volume of the magnesium slag and mixed uniformly. The mixture was stacked at a thickness of 6 m.
(2) A mixture of sludge, kitchen waste and fly ash was stacked on the first layer, and the water content of the mixture was adjusted to 60% so that the fermentation water meets the basic requirements of anaerobic fermentation. At the same time, the carbon-nitrogen ratio was adjusted to be 35:1, pH 5.5, salinity 20%, and composting thickness 3 m, for anaerobic fermentation.
(3) Steps (1)-(2) were repeated alternately and multi-layer composting was performed according to a stacking treatment amount to improve stacking efficiency and total treatment amount.
(4) A bionic swamp cover head was laid on the uppermost layer of the stacked layer, wherein the bionic swamp cover head consists of straw and mushroom dregs mixed according to a volume ratio of 3:2, and the crushed particle size of the two components was 3 cm. During the anaerobic fermentation process, a functional microorganism eluent, a carbon-nitrogen ratio eluent, a pH value adjustment eluent and a high-salt cluent for the lower stacked layer can be transported via the bionic swamp cover head, and at the same time the use of the bionic swamp cover head to adjust the damp-heat energy storage of the bottom stacked layer can be facilitated. A solar membrane for energy collection was provided on the bionic swamp. In the microorganism cluent, the microorganism was an acidogenic anaerobic fermentation microorganism, preferably *Pseudomonas fluorescens* and *Xanthomonas campestris* (mixed with equal solution volume). Water was sprayed in an amount of 1.00 m³/m³ material per day for 50 days.

(5) An induction probe was provided at the bottom of the bionic swamp cover head to feed back the temperature and humidity of the fermentation stack in time, and when the temperature is too high or too low; the condition was controlled by delivering the eluent at a certain temperature. The temperature was maintained at 30° C. and humidity was maintained at 60%.

Experiment I: Experiment on Solid Waste Modified by a Microorganism Synergistically with Coal Gangue Material as Substrate Experiment method: The organic acid produced by microorganisms in the process of growth and reproduction can not only reduce the pH value in the soil environment but also directly release the phosphorus in the fixed-state phosphate into the soil. This experiment is mainly to study the process parameters of modifying solid waste magnesium slag by a microorganism synergistically with coal gangue. The specific method is described in Example 3. The solid waste is modified by comparing the proportions of magnesium slag, coal gangue and vinegar dregs with different proportions, and the phosphate-solubilizing bacterium and *Xanthomonas* spp. to form a substrate for plant growth and cultivation. After 35 days of reforming, the substrate water content (%), substrate aeration rate (the maximum volume of heavy oxygen per square meter of the substrate, unit: m³/m²), effective phosphorus content (mg/kg), and organic acid (oxalic acid) content (mg/kg) can be calculated and determined. Each treatment can be averaged in triplicate. *Pseudomonas fluorescens* powder (viable effective bacteria 300 billion cfu/mL) in the control group was purchased from Jiangsu Changzhou Lanling Pharmaceutical Co. Ltd. *Bacillus* wettable powder (effective viable bacteria 1 billion cfu/mL) was purchased from Zhejiang Tonglu Huifeng Biochemical Co. Ltd.

TABLE 1

Solid waste modification experiment table

| Experiment No | Magnesium slag Volume part | Coal gangue Volume part | Vinegar dregs Volume part | Phosphate-solubilizing bacterium | Xanthomonas | pH value |
|---|---|---|---|---|---|---|
| 1 | 100 | 5 | 10 | *Pseudomonas fluorescens*N1 | *Xanthomonas campestris* | 5.5 |
| 2 | 100 | 10 | 10 | *fluorescens fluorescens*NI | *Xanthomonas campestris* | 5.5 |
| 3 | 100 | 15 | 10 | *Pseudomonas fluorescens*N1 | *Xanthomonas campestris* | 5.5 |
| 4 | 100 | 5 | 20 | *Pseudomonas fluorescens*N1 | *Xanthomonas campestris* | 5.5 |
| 5 | 100 | 10 | 20 | *Pseudomonas fluorescens*N1 | *Xanthomonas campestris* | 5.5 |

TABLE 1-continued

Solid waste modification experiment table

| Experiment No | Magnesium slag Volume part | Coal gangue Volume part | Vinegar dregs Volume part | Phosphate-solubilizing bacterium | Xanthomonas | pH value |
|---|---|---|---|---|---|---|
| 6 | 100 | 15 | 20 | Pseudomonas fluorescensN1 | Xanthomonas campestris | 5.5 |
| 7 | 100 | 5 | 30 | Pseudomonas fluorescensN1 | Xanthomonas campestris | 5.5 |
| 8 | 100 | 10 | 30 | Pseudomonas fluorescensN1 | Xanthomonas campestris | 5.5 |
| 9 | 100 | 15 | 30 | Pseudomonas fluorescensNI | Xanthomonas campestris | 5.5 |
| Control 1 | 100 | 10 | 30 | Pseudomonas fluorescensNI | — | 5.5 |
| Control 2 | 100 | 10 | 30 | — | Xanthomonas campestris | 5.5 |
| Control 3 | 100 | 10 | — | Pseudomonas fluorescensN1 | Xanthomonas campestris | 5.5 |
| Control 4 | 100 | — | 30 | Pseudomonas fluorescensN1 | Xanthomonas campestris | 5.5 |
| Control 5 | 100 | 10 | 30 | Pseudomonas fluorescensNI | Xanthomonas campestris | 5.0 |
| Control 6 | 100 | 10 | 30 | Pseudomonas fluorescensN1 | Xanthomonas campestris | 6.0 |
| Control 7 | 100 | 10 | 30 | Bacillus | Xanthomonas campestris | 5.5 |
| Control 8 | 100 | 10 | 30 | Pseudomonas fluorescens powder | Xanthomonas campestris | 5.5 |

TABLE 2

Influence of different modification conditions on the indexes of solid waste-reformed substrate

| Experiment No | Effective phosphorus content (mg/kg) | Oxalic acid content (mg/kg) | Substrate water content (%) | Substrate aeration rate ($m^3/m^2$) |
|---|---|---|---|---|
| 1 | 765.43 | 13.43 | 47.2 | 0.39 |
| 2 | 818.48 | 14.32 | 48.3 | 0.41 |
| 3 | 830.09 | 14.56 | 50.0 | 0.41 |
| 4 | 770.97 | 13.52 | 48.5 | 0.38 |
| 5 | 829.43 | 14.66 | 50.4 | 0.42 |
| 6 | 830.23 | 14.78 | 52.8 | 0.43 |
| 7 | 795.36 | 13.11 | 55.4 | 0.43 |
| 8 | 880.61 | 15.60 | 58.3 | 0.45 |
| 9 | 873.50 | 14.69 | 57.5 | 0.43 |
| Control 1 | 823.43 | 12.32 | 51.4 | 0.19 |
| Control 2 | 765.01 | 11.47 | 52.1 | 0.20 |
| Control 3 | 754.57 | 13.45 | 42.3 | 0.17 |
| Control 4 | 330.40 | 10.22 | 51.4 | 0.13 |
| Control 5 | 570.47 | 14.43 | 52.6 | 0.31 |
| Control 6 | 475.78 | 10.13 | 53.9 | 0.30 |
| Control 7 | 612.52 | 11.23 | 49.9 | 0.33 |
| Control 8 | 872.89 | 14.93 | 58.02 | 0.41 |

Experimental Results

Different coal gangue contents affect the effective phosphorus content of the substrate and the production of organic acids. All other experiments had higher effective phosphorus content in the substrate compared to Control 4 without added coal gangue. Among them, best results were obtained when the coal gangue content was 10-15 volume parts. The adsorption capacity of coal gangue modified by microorganisms is very strong, and it directly releases phosphorus from the fixed-state phosphate. The content of organic acids (glycolic acid) was also highest in Experiment 8. Glycolic acid is the most representative type of organic acid and one of the important organic acids required for plant growth. By synergistically modifying the solid waste magnesium slag and coal gangue with Pseudomonas fluorescens (Control 8 or strain Experiment 8 of this application) and Xanthomonas, the organic acids in the solid waste can be released, thereby promoting plant growth. In addition, Control 7 showed that, in comparison with the other microorganisms, the effect of phosphate-solubilizing and organic acid-releasing thereof was not as good as that of using the combination of Pseudomonas fluorescens+Xanthomonas of this application, and the comprehensive physical and chemical properties of the improved solid waste-reformed substrate were superior to those of using one of the microorganisms alone, such as Controls 1 and 2.

Different pH values have different effects on the phosphate-solubilizing effect of the strains. After 30 days of modification on the solid waste, for the effective phosphorus content compared to Controls 5 and 6, the effect of phosphate-solubilizing as well as the production of organic acids was weaker at pH 5.0 and 6.0, and a higher amount of dissolved phosphorus could be produced at pH 5.5. Experiment 8 had the highest effective phosphorus content and organic acid content at pH 5.5. The results showed that the effect of phosphate-solubilizing and organic acid production is good in the acidic solid waste substrate environment.

This application is the first to use magnesium slags as a hydrophobic raw material and vinegar dregs as a hydrophilic raw material, and through the reasonable proportioning of the two materials, combined with the adjustment of particle size, to achieve the water content and aeration of the substrate suitable for plant cultivation. The comparative example showed that the volume ratio of magnesium slags and vinegar dregs at 100:30 can achieve the best effect on the water content and aeration of the substrate. Compared with the magnesium slag solid waste without coal gangue, the substrate aeration can be significantly reduced, and compared with the magnesium slag solid waste without vinegar dregs, the substrate water content can be also significantly reduced.

Experiment II: Orthogonal Design Analysis Affecting the Remediation Capacity of Solid Waste-Reformed Substrate Experiment method: to find the factors and optimal combinations affecting the remediation capacity of the solid waste-reformed substrate on heavy metal contaminated soil and the phosphate-solubilizing effect of effective phosphorus, and to provide the theoretical basis for the optimal combination of remediation technologies after solid waste reforming. The three conditions of material particle size A (2 mm for level 1, 3 mm for level 2, and 5 mm for level 3), the amount of coal gangue addition B (percentage of magnesium slag volume) (10% for level 1, 13% for level 2, and 15% for level 3), and phosphate-solubilizing bacterium dosage C (0.50 m$^3$/m$^3$ for level 1, 0.80 m$^3$/m$^3$ for level 2, and 1.00 m$^3$/m$^3$ for level 3) were taken as the variables, the heavy metal lead removal rate and effective phosphorus content as indicators to select the optimal combination, L9 (33) orthogonal table. The lead removal rate was specifically prepared to simulate lead-contaminated soil. Based on 30% water content, a certain concentration of Pb(NO$_3$)$_2$ solution was added to the substrate soil, and the Pb content in the soil was controlled to be 200 mg/L. The mixture was homogenized and placed in a constant temperature incubator to stabilize for 90 d. The contaminated soil was taken out every 10 d, and added with deionized water, and the relative water content of the soil was controlled to be about 30% by the mass method. Various materials of the experiment levels mentioned above were added to simulate the remediation for 30 days and determine the Pb$^{2+}$ concentration and effective phosphorus content. The removal rate of heavy metal lead=(C0-C1)/C0, where C0-the lead concentration (mg/L) of the initial solution before the experiment; C1-the lead concentration (mg/L) of the residue after adsorption. Each treatment can be averaged in triplicate.

TABLE 3

Orthogonal design table affecting the remediation capacity of solid waste-reformed substrate

| A Material particle size | B Amount of coal gangue addition | C Phosphate-solubilizing bacterium dosage | Lead removal rate (%) | Effective phosphorus (mg/kg) | |
|---|---|---|---|---|---|
| 1 | 1 | 1 | 75.4 | 854.09 | |
| 1 | 2 | 2 | 76.6 | 859.23 | |
| 1 | 3 | 3 | 89.1 | 878.78 | |
| 2 | 1 | 2 | 69.9 | 609.8 | |
| 2 | 2 | 3 | 93.8 | 873.8 | |
| 2 | 3 | 1 | 83.5 | 735.5 | |
| 3 | 1 | 3 | 71.2 | 764.49 | |
| 3 | 2 | 1 | 89.4 | 751.27 | |
| 3 | 3 | 2 | 94.5 | 779.86 | |
| K1 | 80.37 | 72.17 | 82.77 | B > A > C | |
| K2 | 82.40 | 86.60 | 80.33 | | |
| K3 | 85.03 | 89.03 | 84.70 | | |
| R | 4.67 | 16.87 | 4.37 | | |
| Optimum level of lead removal rate | A3 | B3 | C3 | | |
| K1 | 864.03 | 742.79 | 780.29 | A > C > B | |
| K2 | 739.70 | 828.10 | 749.63 | | |
| K3 | 765.21 | 798.05 | 839.02 | | |
| R | 124.33 | 85.31 | 89.39 | | |
| Optimum level of effective phosphorus | A1 | B2 | C3 | | |

Experiment Results: as can be seen from the table above, through the study we have concluded that the factors affecting the remediation capacity of solid waste-reformed substrate are mainly based on the particle size of material A, the amount of coal gangue addition B, and the phosphate-solubilizing bacterium dosage C. The optimal scheme affecting the remediation capacity of solid waste-reformed substrate for heavy metal lead pollution was A3B3C3, i.e., a mixed substrate of 5 mm crushed particle size, 15% coal gangue addition, and 1.00 m$^3$/m$^3$ phosphate-solubilizing bacterium dosage. The optimal scheme for the phosphate-solubilizing effect of solid waste-reformed substrate is A1B2C3, i.e. a mixed substrate of 2 mm particle size, 13% coal gangue addition, and 1.00 m$^3$/m$^3$ phosphate-solubilizing bacterium dosage.

The order of influence of each factor is the ability to remedy heavy metal lead pollution: B (amount of coal gangue addition)>A (crushed particle size)>C (phosphate-solubilizing bacterium dosage). The phosphate-solubilizing effect of the solid waste-reformed substrate: A (crushed particle size)>C (phosphate-solubilizing bacterium dosage)>B (amount of coal gangue addition).

Experiment III: Influence of Phosphorus Ore Powder on the Promotion of Phosphate-Solubilizing by Phosphate-Solubilizing Bacterium Experiment method: this experiment mainly studied the influence of added phosphorus ore powder on the promotion of phosphate-solubilizing by phosphate-solubilizing bacterium. The specific method refers to Example 5, where the other parameter variables remain unchanged and only the amount of phosphorite powder addition is varied. By comparing the addition of different proportions of phosphorus ore powder (the amount of phosphorus ore powder addition is the percentage by volume of the total material of magnesium slag, coal gangue, and vinegar dregs), using the strain of phosphate-solubilizing bacterium and *Xanthomonas* spp. synergistically, the solid waste can be modified to form a substrate for plant growth and cultivation and the parameters of the influence of phosphorus ore powder on the promotion of phosphate-solubilizing by phosphate-solubilizing bacterium can be derived. Among them, the remediation was simulated for 30 days, and the effective phosphorus content was determined. Each treatment can be averaged in triplicate.

TABLE 4

Influence of the amount of different phosphate ore powder addition on the promotion of phosphate-solubilizing by phosphate-solubilizing bacterium

| Experiment No | Amount of phosphorus ore powder addition Total material volume % | Effective phosphorus content (mg/kg) |
|---|---|---|
| 10 | 5 | 878.97 |
| 11 | 8 | 923.65 |
| 12 | 10 | 891.01 |
| 13 | 13 | 889.92 |

Experiment Results: this application concludes that the addition of a certain amount of phosphorus ore powder can further promote the efficacy of the phosphate-solubilizing bacterium, which can further degrade the insoluble phosphorus in its ore powder into soluble phosphate, which can be used as a substrate together with the solid waste, and provide sufficient elements for the plant cultivation substrate. The addition of phosphate rock powder in this experiment has a significant effect on the promotion of phosphate-solubilizing by phosphate-solubilizing bacterium. With other parameters unchanged, only the amounts of phosphate rock powder additions were changed. By comparing the addition of different proportions of phosphorus ore powder (the amount of phosphorus ore powder addition is the percentage by volume of the total material of magnesium slag, coal gangue, and vinegar dregs), using the strain of phosphate-solubilizing bacterium and *Xanthomonas* spp. synergistically, the solid waste can be modified to form a substrate for plant growth and cultivation and the parameters of the influence of phosphorus ore powder on the promotion of phosphate-solubilizing by phosphate-solubilizing bacterium are derived. As in Experiment 11, when the amount of phosphate rock powder addition was 8%, the effect of phosphate-solubilizing was the best, and when it exceeded 8%, the effect of phosphate-solubilizing was not significantly increased. In production practice, a certain amount of phosphate rock powder can be added in combination with cost considerations to further promote the efficacy of phosphate-solubilizing bacterium.

Experiment IV: Optimization Scheme for Solid Waste Combination Based on Full Bionic Simulation Experiment method: the solid waste combination based on full bionic simulation of this application, in combination with the production of organic acids by microorganisms in the process of growth and reproduction, can not only reduce the pH value in the soil environment but also directly release the phosphorus in the fixed-state phosphate into the soil. This experiment mainly studies the solid waste combination based on full bionic simulation and optimizes the process parameters. The specific method is referred to Example 6. By comparing different ratios and combinations of modified solid wastes to form a substrate for plant growth and cultivation, we calculated and measured the effective phosphorus content (mg/kg) and organic acid (glycolic acid) content (mg/kg) in the bottom solid waste layer after 60 days of transformation. Each treatment can be averaged in triplicate.

results were obtained when the volume ratio of kitchen waste: sludge: fly ash (or desulphurization ash) was 100:50:30. The adsorption capacity of coal gangue modified by microorganisms is very strong, and it directly releases phosphorus from the fixed-state phosphate. The content of organic acids (glycolic acid) was also highest in Experiment 14. Glycolic acid is the most representative type of organic acid and one of the important organic acids required for plant growth. By synergistically modifying the solid waste with microorganisms and a full-bionic swamp, the organic acids in the solid waste can be released, thereby promoting plant growth.

During the reaction process, we found that the control of water content, salinity, and carbon-nitrogen ratio in the full bionic simulation swamp reaction is very important, and its effect on the fermentation effect of solid waste is different. After 60 days of reforming the solid waste test field, it was concluded that the highest fermentation and decomposition effect was achieved when the carbon-nitrogen ratio was adjusted to 35:1, salinity was 20%, and water content was 60%. It indicates that the phosphate-solubilizing and promotion of organic acid production in an acidic solid waste substrate environment is effective. In the process, the effective phosphorus content and acid production are both high. At the same time, the parameter could maintain the acidic environment and promote the persistent decomposition effect of microorganisms. Too high carbon-nitrogen ratio is not conducive to microbial acid production reaction, 25-35:1 is able to produce more organic acids, thus promoting the decomposition of solid waste. Too high and too low salt concentrations also affect the process of acid production. When the salt concentration is about 20%, the effect of acid production is better. The water content of biomimetic simulated swamp mixture is also an important factor affecting the microbial fermentation reaction. When the water content is 60%, the fermentation reaction of solid waste is superior.

TABLE 5

Solid waste combination optimization experiment based on full bionic simulation

| Experiment No | Kitchen waste Volume part | Sludge Volume part | Fly ash Volume part | Water content % | Carbon-nitrogen ratio | Salinity % | Effective phosphorus content (mg/kg) | Oxalic acid content (mg/kg) |
|---|---|---|---|---|---|---|---|---|
| 14 | 100 | 50 | 30 | 60 | 35:1 | 20 | 853.21 | 14.87 |
| 15 | 100 | 50 | 50 | 60 | 35:1 | 20 | 834.02 | 14.33 |
| 16 | 100 | 50 | 10 | 60 | 35:1 | 20 | 810.35 | 13.43 |
| 17 | 100 | 40 | 10 | 60 | 35:1 | 20 | 798.03 | 13.59 |
| 18 | 100 | 10 | 20 | 60 | 35:1 | 20 | 674.25 | 10.83 |
| 19 | 100 | 10 | 40 | 60 | 35:1 | 20 | 678.02 | 10.00 |
| 20 | 100 | 10 | 50 | 60 | 35:1 | 20 | 690.34 | 11.01 |
| Control 9 | 100 | 50 | — | 60 | 35:1 | 20 | 776.20 | 11.08 |
| Control 10 | 100 | — | 30 | 60 | 35:1 | 20 | 650.35 | 10.46 |
| Control 11 | 100 | 50 | 30 replaced with desulfurized ash | 60 | 35:1 | 20 | 861.82 | 14.39 |
| Control 12 | 100 | 50 | 30 | 80 | 35:1 | 20 | 673.03 | 10.31 |
| Control 13 | 100 | 50 | 30 | 40 | 35:1 | 20 | 653.93 | 10.46 |
| Control 14 | 100 | 50 | 30 | 60 | 40:1 | 20 | 664.38 | 10.45 |
| Control 15 | 100 | 50 | 30 | 60 | 25:1 | 20 | 804.23 | 13.01 |
| Control 16 | 100 | 50 | 30 | 60 | 35:1 | 10 | 626.94 | 11.25 |
| Control 17 | 100 | 50 | 30 | 60 | 35:1 | 30 | 796.03 | 12.93 |

Experimental Results

Different parameters of full bionic simulation can effective phosphorus content and organic acid production of solid waste. Compared with Controls 9 and 10 without adding sludge or fly ash (or desulfurized ash), the effective phosphorus content of solid waste decomposed by the full bionic simulation formula of other experiments is higher. The best Experiment V: Optimization Scheme of Full Bionic Cover Head Combination Experiment method: the full bionic cover head combination of this application works with microorganisms to produce organic acids during growth and reproduction. Using a bionic simulation of the natural process of organic carbonite production, combined with the conditions of biofermentation for acid production, and using the carbon-nitrogen ratio, pH, and salinity in the waste liquid, acid production can be regulated. This experiment is mainly to study the combination of a full bionic cover head to optimize the conditions of process parameters. Specifically, the bionic swamp cover head was laid in the uppermost layer of the solid waste pile, and the environment was adjusted by adjusting the components of the bionic swamp cover head, so as to control the anaerobic fermentation environment of the bionic swamp mixture and solid waste in the lower layer, and to provide the most suitable anaerobic fermentation conditions. The specific method is referred to Example 6. The conditions suitable for solid waste fermentation were derived by comparing different ration combinations of cover heads in the uppermost layer of the bionic swamp mixture. Each treatment can be averaged in triplicate. After 60 days of fermentation, the ammonia nitrogen content (mg/L) in the mixture layer and the effective phosphorus content (mg/kg) in the bottommost solid waste layer were determined.

TABLE 6

Simulation parameter optimization experiment table for full bionic cover head

| Experiment No | Straw volume part | Mushroom dregs volume part | Crushed particle size cm | Temperature | Humidity % | Ammonia nitrogen mg/L | Effective phosphorus content (mg/kg) |
|---|---|---|---|---|---|---|---|
| 21 | 3 | 2 | 3 | 30 | 60 | 665.61 | 853.21 |
| 22 | 3 | 1 | 3 | 30 | 60 | 613.43 | 846.38 |
| 23 | 1 | 1 | 3 | 30 | 60 | 600.38 | 814.29 |
| 24 | 1 | 3 | 3 | 30 | 60 | 610.24 | 841.53 |
| 25 | 2 | 3 | 3 | 30 | 60 | 634.01 | 851.28 |
| Control 18 | 3 | 2 | 5 | 30 | 60 | 635.90 | 828.39 |
| Control 19 | 3 | 2 | 3 | 40 | 60 | 528.92 | 736.94 |
| Control 20 | 3 | 2 | 3 | 30 | 40 | 528.01 | 728.22 |
| Control 21 | 3 | 2 | 3 | 30 | 80 | 562.35 | 730.26 |
| Control 22 | 3 | — | 3 | 30 | 60 | 503.35 | 669.45 |
| Control 23 | — | 2 | 3 | 30 | 60 | 525.73 | 673.57 |

Experiment Results: the simulated bionic cover head can be moderately insulated and moisturized. Anaerobic fermentation conditions can be further adjusted by controlling the temperature of the cover head. Because in the anaerobic fermentation process, a lot of heat will be produced. The simulation bionic cover head can maintain a certain temperature, the temperature should be controlled to be not too high to affect the microbial fermentation. Humidity regulation is also a key factor in further maintaining the anaerobic fermentation of solid waste. Through the experiment, we found the suitable temperature and humidity affecting the fermentation of the bionic swamp mixture, that is, the results were better at 30° C. temperature and 60% humidity, and the conditioning was suitable for putrefaction and fermentation of the lower bionic swamp mixture, with ammonia nitrogen release as high as 665.61 mg/L, and effective phosphorus release from the solid waste as high as 853.21 mg/kg.

The simulated bionic cover head of this application is obtained through a large number of experiments and comparisons. The optimal ratio of straw to mushroom dregs is 3:2 by volume, and the fermentation effect is optimal when the crushed particle size is 3 cm. With reference to Controls 22 and 23, the simulated bionic cover head of this application had a superior insulation and moisturizing and fermentation-promoting effect after combination compared to the simulated bionic cover head composed by adding one ingredient.

While the foregoing is directed to the preferred examples of the present invention, other and further examples of the invention may be devised without departing from the basic scope thereof, and the scope thereof is determined by the claims that follow. Any modifications, equivalent substitutions, improvements, etc. made within the spirit and principles of this application are included within the scope of this application.

The invention claimed is:

1. A method for modifying solid waste by a microorganism synergistically with coal gangue material, comprising the following steps:

(1) adding coal gangue to magnesium slag in an amount of 10-15% by volume of the magnesium slag, mixing thoroughly, sieving to control a particle size of the mixed material to be 2-5 mm, and stacking for 5-10 days;

(2) adding vinegar dregs in an amount of 20-30% by volume of the magnesium slag, mixing thoroughly, and adjusting the pH value to 5.5-6.5 using a wood vinegar liquid; and (3) spraying *Pseudomonas fluorescens* N1 registered in the China General Microbiological Culture Collection Center under the accession number CGMCC No. 23192 or *Pseudomonas fluorescens* N1 registered in the China General Microbiological Culture Collection Center under the accession number CGMCC No. 23192+*Xanthomonas campestris* mixed in an equal solution volume onto the mixed material surface, and spraying water in an amount of 0.50-1.00 $m^3/m^3$ mixed material per day for 30-40 days.

2. The method of claim 1, wherein the solid waste is heavy metal contaminated soil.

3. The method of claim 2, further comprising a step of:
(4) adding phosphate rock powder in an amount of 5-10% by volume of the total materials, and mixing thoroughly, thus creating a substrate for cultivation.

* * * * *